United States Patent [19]

Filips et al.

[11] Patent Number: 4,633,863
[45] Date of Patent: Jan. 6, 1987

[54] ARTERIAL ANCHOR BANDAGE

[76] Inventors: Chester P. Filips, 16401 SW. 142nd Ave., Lot 49, Miami, Fla. 33177; Antonio G. Blanco, 927 SW. 118th Ct., Miami, Fla. 33184

[21] Appl. No.: 780,815
[22] Filed: Sep. 27, 1985
[51] Int. Cl.$^4$ .............................................. A61L 15/00
[52] U.S. Cl. ..................................... 128/165; 604/240
[58] Field of Search ............... 128/165, 154, 158, 132; 604/43, 51, 244, 275, 307, 240

[56] References Cited

U.S. PATENT DOCUMENTS

| | | | |
|---|---|---|---|
| 2,221,758 | 11/1940 | Elmquist | 128/154 |
| 3,782,377 | 1/1974 | Rychlik | 604/307 |
| 4,191,176 | 3/1980 | Spina | 604/51 |
| 4,250,882 | 2/1981 | Adair | 128/154 |

Primary Examiner—Gregory E. McNeill

Attorney, Agent, or Firm—Burns, Doane, Swecker & Mathis

[57] ABSTRACT

An arterial anchor bandage has a transparent bulbous shield which protrudes above a tri-lobed outer covering layer. The bulbous shield has an opening sized to receive the tube from an arterial catheter and has a generally elliptical cross section. A flange at the bottom of the shield prevents the shield from cutting into the skin of the patient. An absorbent layer between the shield and the skin surface provides a wicking function to remove fluids from the area where the arterial catheter enters the patient. A protective sheet covers an adhesive surface of the outer covering layer so that the arterial anchor bandage can be applied as a unit assembly once the catheter has been inserted. Various features of the structure permit its application very close to joints in a patient's anatomy.

7 Claims, 5 Drawing Figures

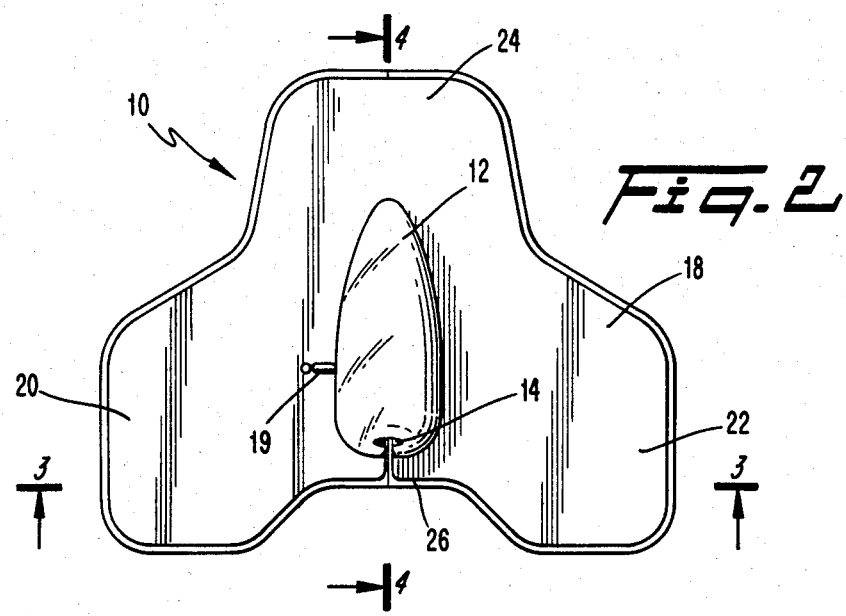
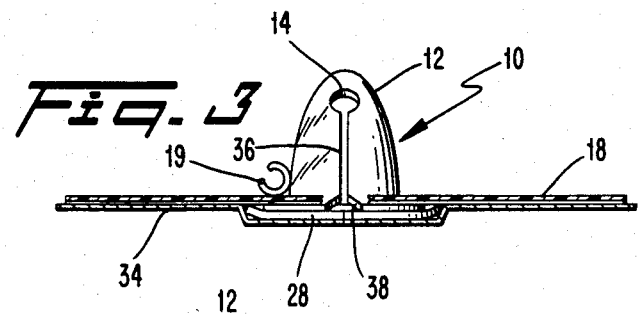
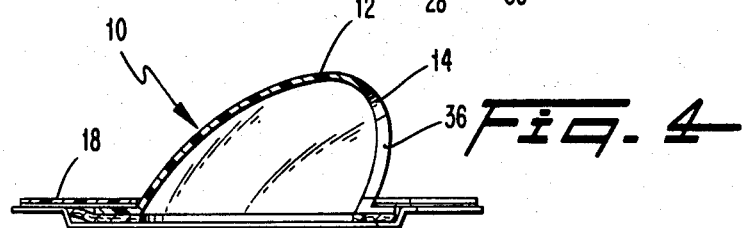
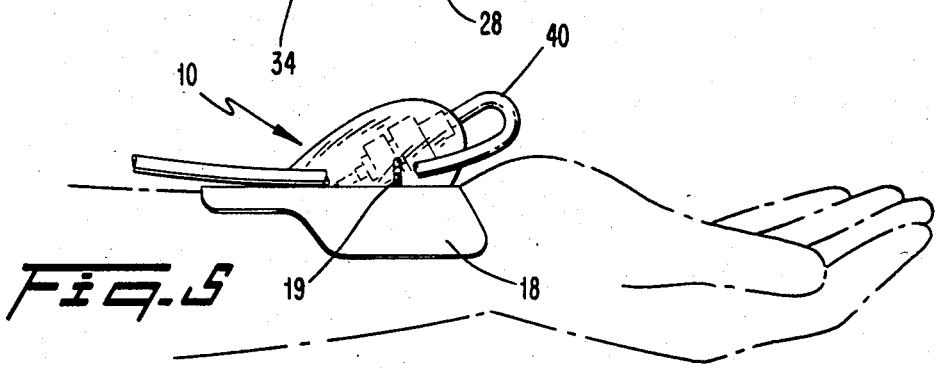

ARTERIAL ANCHOR BANDAGE

BACKGROUND OF THE INVENTION

The present invention relates generally to bandages for holding and positioning devices inserted into arteries. More particularly, the present invention concerns a one-piece assembly for supporting an arterial catheter against dislocation, keeping the incision site clear, and bandaging the area.

In the healing arts there are two different kinds of probes which are inserted into the blood system of a patient: intravenous probes and arterial catheters. These different kinds of probes take their names from the different parts of the human circulation system into which they are inserted, namely arteries and veins. However, the differences between these two kinds of probes are considerably more significant than the mere difference between the names.

Intravenous probes are used for administration of medications, involuntary feeding, and blood transfusions. Arterial catheters are not, however, used for those functions. Quite apart from intravenous probes, arterial catheters are used to provide attending medical staff with important information concerning the patient's circulatory system and its functioning.

For example, arterial catheters help doctors to determine whether a patient is in either a hypertensive crisis or hypotensive crisis during surgery, as well as after surgery. In addition, these arterial catheters allow blood sampling for various purposes, including determination of the blood gas value.

Another important use for arterial catheters is to monitor the positive pulsating pressure in the artery which is dynamic and which is generated by the patient's heart. That positive pulsating pressure creates a different operating environment for the arterial catheter as contrasted to the intravenous probe. More particularly, the intravenous probe operates in veins where the pressure is static and is caused primarily by gravity.

The pressure monitored in the arterial catheter is used to regulate all infusion of blood and drugs administered to the patient. Generally, the arterial catheter is used during serious medical situations such as during the pendency of surgery, during post-operative recovery, and during residence in an intensive care unit of a hospital.

Besides the difference between the location and function of arterial catheters as compared to intravenous probes, the arterial catheters actually have a different construction than do the intravenous probes. Some intravenous probes (called "butterflies") are rigid needles which are very short and which are used in delicate veins. In contrast, the large majority of arterial catheters in use today are of the flexible type. For example, the arterial catheter generally is a two part system having an inner stylet surrounded by a flexible outer sheath made of polytetrafluoroethylene, such as Teflon. The stylet allows the catheter to puncture the skin and enter an artery or vein. Once the catheter has been inserted, the stylet is removed leaving the outer sheath in place within the artery. When the flexible tube which penetrates into the artery has a pressure sensor that is thus placed in intimate association with the blood stream, the catheter can be used to measure blood pressure. The intravenous probe, on the other hand, is typically a rigid needle inserted into a vein.

Since arterial catheters are flexible and since they communicate with a pressure monitoring system, kinks, crimps, and bends in the line can cause changes in the pressure reading. In medical parlance such changes in pressure readings are referred to as positional sensitivity of the arterial catheter. Positional sensitivity occurs more often in an arterial line than in a venous line because of the different character of the musculature of an artery in comparison to a vein. To reduce positional sensitivity the catheter should remain as central to the arterial wall as possible due to the dynamic construction and dilation of the arterial wall in response to the blood flow demands of a patient's body.

Positional sensitivity of the arterial catheter leads to another difference between the arterial catheter and an intravenous probe: the arterial catheter must be capable of rotation about its longitudinal axis, whereas the intravenous probe needs no such rotatability. Rotation of the arterial catheter permits the monitoring equipment to determine whether positional sensitivity is interfering with the clearest readings. Accordingly, bandaging the arterial catheter to the patient involves different requirements than does the intravenous probe.

The different locations of the arteries and the veins in human anatomy are also a factor in the application of arterial catheters to the patient. Generally speaking, arteries are positioned deep within the limbs of a patient whereas veins are located near the skin surface. To insert an arterial catheter, it becomes necessary to locate one of the few areas of the body where arteries pass close to the skin surface. For example, the radial artery which passes through the forearm is near the skin surface along the wrist, the brachial artery which passes through the upper arm is near the skin surface at the crease of the elbow, the femoral artery which passes through the thigh is near the skin surface at the groin, and the dorsalis pedis artery of the foot is near the skin surface at the ankle. Thus, it will be observed that the places where arterial catheters can be inserted are not only limited by are located at awkward areas where limbs also articulate. As a result there are special problems associated with arterial catheters which are not encountered with intravenous probes.

When an arterial catheter has been inserted, there are several highly desirable characteristics that an anchor bandage should provide. The entrance of the catheter into the skin should be subject to visual inspection. The anchor bandage should be rigid so that the arterial catheter will be held in a secure, fixed relationship to the patient. The anchor bandage should provide reliable, prompt application. And, the anchor bandage should be sterile.

In the past, the normal procedure for insertion of an arterial catheter has been to clean and disinfect the skin area around the intended insertion point. Then an incision is made to insert the arterial catheter in the selected artery. With the catheter in place, additional skin penetrations are necessary to suture the arterial catheter into its proper position and location. Thereafter gauze pads are applied to draw drainage from the wound away from the wound and tape is applied to secure the gauze in place. Since the area of cannulation is often located at one of the patient's joints, it is often necessary to secure the limb to a board or other rigid member to prevent inadvertent movement that could cause a positional affect on readings taken from the arterial catheter.

The procedure heretofore used has numerous problems and disadvantages associated therewith. For example, the arterial catheter often is highly positional. In addition, the site of catheter entry into the patient is often obscured and not visible. Typically the procedure to finish the procedure once the arterial catheter has been placed in the artery can consume 3 to 10 minutes or more, depending on the experience of the staff person who installs the catheter. And furthermore, since the arterial catheter is often inserted under conditions which demand great haste, it is not always dressed with sterile materials. In addition, there are a number of different items which must be stocked in order to effect the bandaging of an arterial catheter, all of which require precious storage space.

From the foregoing discussion, it will be apparent that there is a considerable difference between bandages for arterial catheters as compared to intravenous probes. That difference indicates that devices for applying and bandaging of intravenous probes have little or no relevance to arterial anchor bandages. In fact, no prior art arterial anchor bandages are known.

There are of course numerous devices for holding and protecting intravenous probes. For example, it is known to provide a transparent enclosure with a mounting sheet and to use that assembly to enclose an intravenous probe. See for example U.S. Pat. No. 3,900,026 issued to Wagner and U.S. Pat. No. 3,782,377 issued to Rychlik. Other intravenous devices are disclosed in U.S. Pat. No. 2,266,230 issued to Mazzei et al, U.S. Pat. No. 3,288,137 issued to Lund, U.S. Pat. No. 3,782,378 issued to Page, U.S. Pat. No. 4,324,237 issued to Buttaravoli, and U.S. Pat. No. 4,502,477 issued to Lewis. As emphasized, structures associated with intravenous probes are not transferable to use with arterial catheters.

OBJECTS AND SUMMARY OF THE INVENTION

It is a general object of the present invention to provide an arterial anchor bandage for use with arterial catheters.

It is another object of the present invention to provide an arterial anchor bandage which overcomes problems associated with prior procedures for securing arterial catheters.

It is also an object of the present invention to provide an arterial anchor bandage which provides continual visual inspection of the site surrounding entry of the arterial catheter into the patient.

It is a further object of the present invention to provide an arterial anchor bandage which provides a definite fixed position for an arterial catheter relative to a patient.

It is yet another object of the present invention to provide an arterial anchor bandage which permits rotation of an arterial catheter without removing the bandage to check on positionality of the arterial catheter.

It is a still further object of the present invention to provide an arterial anchor bandage which can applied in less time than earlier procedures and which eliminates the need for suturing the arterial catheter in place while maintaining visual surveillance of the catheter.

A further object of the present invention is to provide an arterial anchor bandage having porosity and wicking characteristics which draw fluids from the entry site while permitting air circulation.

Yet another object of the present invention is to provide an arterial anchor bandage which can be applied around an arterial catheter line as an assembly.

A further object of the present invention is to provide an arterial anchor bandage which holds an extension of an arterial catheter such that the stress area in routing the cannula is moved outside the bandage and away from the point where the catheter enters the body to reduce stress on the patient's body.

A still further object of the present invention is to provide an arterial anchor bandage which holds an extension of the catheter such that it does not allow the catheter to slip out of place unless there is a direct application of downward pressure during the application of removal of the anchoring bandage.

An arterial anchor bandage which provides the foregoing objects includes a transparent bulbous shield having a generally planar flange and being provided with an opening sized to receive the tube of an arterial catheter. A slit extends from the opening to the flange to provide a means for attaching the arterial anchor to the arterial catheter. Surrounding and underlying the flange of the shield is a layer of absorbent material having wicking capabilities and having a central aperture which is substantially coextensive with the internal periphery of the flange. The absorbent material is effective to draw fluids away from the open area surrounded by the flange and covered by the bulbous shield. In addition, the arterial anchor includes an outer covering with an adhesive surface for application to the patient. The outer covering has a central opening through which the bulbous shield protrudes. The adhesive surface of the covering securely attaches the covering both to the flange of the bulbous shield and to the absorbent layer so that the assembly is held together as a unit. The adhesive layer of the outer covering has a releasable protective layer which can be peeled off when it is time to use the assembly.

Those portions of the outer layer, the absorbent layer and the protective layer in alignment with the slit in the bulbous shield are also slit so that an arterial anchor tube can be positioned in the conformingly sized opening in the bulbous shield without being disconnected from the arterial catheter.

In order to make the bulbous shield stiff and in order to help the bulbous shield anchor the arterial catheter, the portion of the bulbous shield adjacent to the slit can be thicker than the other portions of the shield.

As noted, arterial catheters and the bandages for them are typically located in skin areas near an articulatable joint of the patient's body. To permit reasonable amounts of mobility in the joint without interference with the arterial catheter, the bulbous shield meets the flange with an acute angle in the area of the slit. This arrangement moves the bulbous shield inwardly and away from the crease of a joint.

Healing of a wound is normally accelerated when the wound is exposed to air. To facilitate the circulation of air in the vicinity of the arterial catheter, the outer cover is preferably made from a porous material. Alternatively, the outer cover may be provided with a plurality of pores through which air has a reasonable ability to circulate.

The outer covering is also provided with a unique shape. The shape includes three lobes, a lobe on each side of the bulbous shield and a third lobe extending away from the bulbous shield on the side opposite from the slit. With this arrangement, the outer covering can be easily applied to the patient's skin without interfering with the joint movement.

BRIEF DESCRIPTION OF THE DRAWINGS

The foregoing as well as many other objects and advantages of the present invention will be apparent to those skilled in the art when this specification is read in conjunction with the attached drawings wherein like reference numerals have been applied to like elements and wherein:

FIG. 2 is a plan view of an arterial anchor bandage according to the present invention;

FIG. 3 is cross-sectional view taken along the line 3—3 of FIG. 2;

FIG. 4 is a cross-sectional view taken along the line 4—4 of FIG. 3; and

FIG. 5 is a pictorial view of the arterial anchor bandage of the present invention applied to an arterial catheter.

DESCRIPTION OF THE PREFERRED EMBODIMENT

Figure 1:
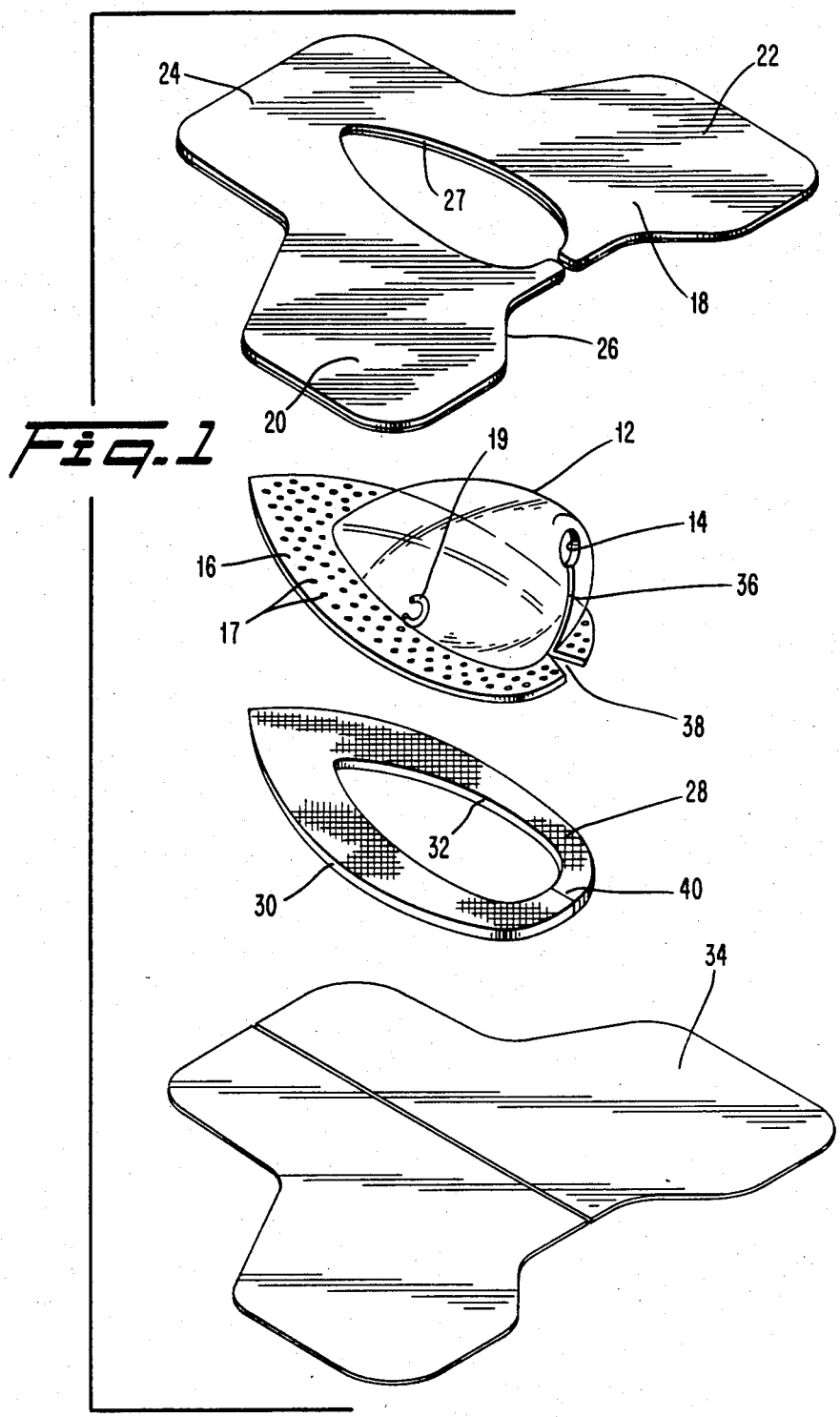
FIG. 1 is an exploded view of the layers of the arterial anchor bandage according to the present invention.

Turning now to FIG. 1, an exploded view of an arterial anchor bandage 10 according to the present invention is shown. The arterial anchor bandage 10 is an assembly of several layers and elements. A bulbous shield 12 constructed from a transparent material is the most conspicuous feature of the arterial anchor bandage 10.

This bulbous shield is proportioned lengthwise so that it will be long enough to accommodate the coupling to an arterial catheter within the cavity defined by the bulbous shield. The bulbous shield is proportioned laterally so that it will be wide enough to accommodate the coupling to the arterial catheter within the cavity and to permit visual inspection around the arterial catheter of the region beneath the catheter. However, the lateral width of the bulbous shield is selected to be much less than the longitudinal length. This condition is important since it reduces the amount of deformation which is sometimes necessary if the bulbous shield is to easiy conform to the contour of the patient's skin.

At one end, the bulbous shield has a generally circular opening 14. The height of the bulbous shield is selected so that this circular opening 14 is elevated above the plane of the bottom of the bulbous shield by a distance which provides the desired angular orientation of an arterial catheter. Typically, an arterial catheter is positioned at an angle of 30° or 45° relative to the plane of the bottom of the bulbous shield.

Injection molding and thermoforming are among the suitable processes by which the bulbous shield can be manufactured. In addition, the bulbous shield can be fashioned from any suitable plastic material which can provide a transparent enclosure. Transparency is important since the bulbous shield functions not only as an enclosure and anchor for the arterial catheter but also as a window through which visual inspection may be made of the catheter, the entrance of the catheter into the body, and the condition of the skin surface immediately around the arterial catheter.

At the bottom of the bulbous shield and surrounding the cavity defined by the bulbous shield, there is a generally planar flange 16 which extends outwardly away from an inner peripheral edge of the bulbous shield. This flange 16 is preferably formed so as to be an integral part of the bulbous shield and is fabricated from the same material. The flange 16 effectively prevents any sharp edge of the bulbous shield from being in direct contact with a patient's skin. The thickness of the bulbous shield and the associated flange are selected so that the generally planar flange can conform to the curvature of a patient's skin in the vicinity of the arterial catheter. In this connection, the smoothly curved shape of the bulbous portion of the bulbous shield aids the flange in conforming to the skin surface since the bulbous portion can deform as necessary. Another factor in selecting the skin thickness is that the bulbous portion of the bulbous shield must be sufficiently stiff to securely anchor the arterial catheter in its position when the bandage is in use.

As best seen in FIG. 1, the flange 16 of the bulbous shield 12 is provided with a plurality of openings or pores 17. If desired, these pores may be randomly positioned. The pores 17 aid the circulation of air through the bandage to promote healing.

Another feature of the bulbous shield 12 is the presence of a tube clip 19 on the side of the bulbous portion and adjacent to the flange 16. The tube clip 19 has a C-shaped configuration and may be open to the side. This clip 19 preferably covers an arc larger than 180° so that a tube received in the clip 19 will be retained thereby. In addition, the interior opening of the clip 19 is sized to approximately conform to the external dimension of conventional tubing ordinarily connected with an arterial catheter.

Surrounding the bulbous shield is the outer covering layer 18 of the arterial anchor bandage 10 (see FIG. 2). This outer covering layer 18 can be fabricated from any conventional adhesive sheet material having a surface to which an adhesive is applied. Preferably, an adhesive sheet material having a porous structure permeable to air is used. However, in the event that the adhesive sheet is normally impermeable to air, then the adhesive sheet should be provided with a plurality of pores to permit air to pass thereacross. The purpose of air permeability is to permit air to reach the area of the wound where the arterial catheter enters the skin since air aids in healing.

The outer covering layer 18 has a three lobed shape with the bulbous shield positioned between two of the lobes 20, 22 and with the third lobe 24 in longitudinal alignment with the bulbous shield. With the two side lobes 20, 22 positioned transversely of the bulbous shield, the side lobes are located to wrap the arterial anchor bandage 10 to the patient's body contour. In addition, due to the large surface area of the side lobes relative to the bulbous shield and the adhesive surface, the side lobes 20, 22 securely locate the arterial anchor bandage 10. The third lobe 24 also has a relatively large surface area. But, with the location of the third lobe in longitudinal alignment with the bulbous shield, the third lobe 24 can be used to partially adhere the arterial anchor bandage 10 to the patient while the arterial catheter is secured to the arterial anchor bandage 10.

Another feature of the shape of the outer covering layer 18 is the presence of a recess 26 in longitudinal alignment with the bulbous shield. This recess conveniently permits the arterial anchor bandage 10 to be positioned close to the skin crease at a patient's joint. As noted above, the common body locations for attachment of an arterial catheter are adjacent to articulatable joints of the human body. In fact, the left wrist is the more common location for placement of an arterial catheter. This fact coupled with the desirability of running the tube connected to the catheter between the patient's arm and his body are the reason that the tube clip 19 is positioned on the left side of the arterial anchor bandage 10 as seen in FIG. 2.

Near the central portion of the outer covering layer 18 is a cutout 27 (see FIG. 1) which is sized to receive the bulbous portion of the bulbous shield. Preferably, the cutout 27 closely conforms to the external periphery of the bulbous portion of the bulbous shield adjacent to the flange 16 (see FIG. 2). With this arrangement, when the arterial anchor bandage 10 is assembled, the adhesive on the outer covering layer 18 attaches the flange 16 to the outer covering layer 18, and thus the outer covering layer 18 and the bulbous shield become adhesively attached to one another.

Beneath the flange 16 (see FIG. 1), a layer 28 of absorbent gauze-like material is provided. This absorbent layer 28 has an external periphery 30 and an internal periphery 32. The external periphery 30 of the absorbent layer 28 is proportioned to be slightly larger than the external periphery of the flange 16. In this manner the absorbent layer 28 extends slightly beyond the lateral projection of the flange 16 so that the absorbent layer 28 can be adhesively bonded to the adhesive layer on the bottom of the outer covering layer 18. As a result, the single adhesive layer of the outer covering layer 18 is effective to hold the entire bandage together as a single assembly.

The internal periphery 32 of the absorbent layer 28 is sized to extend just inside the internal peripheral contour of the flange 16. This relationship ensures that the flange 16 will not be in direct contact with the patient's skin. This relationship further enables the absorbent layer 28 to be exposed to the cavity defined by the bulbous shield. And with the absorbent layer 28 extending beyond both the inner and outer peripheries of the flange 16, the absorbent layer 28 is also effective to permit circulation of air from the outer covering layer 18 to the cavity. If desired, the bottom of the absorbent layer 28 may be provided with an adhesive strip. Such an additional adhesive strip may be desirable in some applications to further enhance the anchoring characteristics of the arterial anchor bandage 10.

Under the outer covering layer 18 and the absorbent layer 28 is a protective sheet 34 (see FIG. 3). This protective sheet 34 contacts the adhesive coating on the outer covering layer 18 which is not connected to the absorbent layer 28 or the flange 16. As a result, the protective sheet 34 prevents the arterial anchor bandage 10 from being adhesively connected with anything until an affirmative decision is made that the bandage is to be attached. As illustrated, the protective sheet 34 extends slightly beyond the peripheral edge of the outer covering layer 18. It may however be more convenient for fabrication purposes to have the protective sheet 34 be coextensive with the peripheral edge of the outer covering layer 18.

It will also be noted from FIG. 3 that there is a slit 36 which extends vertically from the circular opening 14 to the flange 16 of the bulbous shield. It will also be observed that the bottom edge of the slit 36 is provided with a V-shaped notch 38. The slit 36 permits the arterial anchor bandage 10 to be separated so that the tube of an arterial catheter can be positioned in the circular opening 14. The V-shaped notch 38 helps guide the tube of an arterial catheter into the slit 36 and also positions the tube while the arterial anchor bandage 10 is being connected thereto. To facilitate the attachment of the tube to the arterial anchor bandage 10, the absorbent layer 28 and the protective sheet 34 also are slit at a position 40 (see FIG. 1) in alignment with the slit 36. Such an arrangement avoids any need to disconnect the arterial catheter from the associated tube in order to apply the arterial anchor bandage 10.

As best seen in FIG. 4, the bulbous portion of the bulbous shield may have a generally elliptical contour where the major axis of the generally elliptical section is inclined relative to the plane containing the flange 16. In addition, the circular opening 14 is also in general alignment with the major axis of the generally elliptical section. The inclined major axis coupled with the planar flange 16 creates an acute angle between the flange 16 and the bulbous shield at the slit 36. That acute angle permits the external peripheral edge of the flange 16 to be in general vertical alignment with the rearmost part of the bulbous portion of the bulbous shield. As a result, the orientation of the bulbous shield permits the arterial anchor bandage 10 to be located quite close to a crease at a patient's joint while maintaining the presence of a flat flange 16 to avoid cutting into the patient's skin with an edge of the bulbous shield.

Ordinarily, the arterial anchor bandage 10 will be packaged in a sterile container so that it is ready for immediate use. That container can be a suitable conventional envelope.

In use, an arterial catheter is inserted into the artery of the patient. Then, rather than suture the catheter in place, the arterial anchor bandage 10 of the present invention is applied. That application involves removing the arterial anchor bandage 10 from its sterile package and positioning the tube attached to the arterial catheter in the notch 38 (see FIG. 3) at the bottom end of the slit 36. Then the sides of the flange 16 are pressed apart so that the tube can be slid up the slit 36 and into the circular opening 14. When the tube is in the circular opening 14, the protective sheet 34 can be removed from the arterial anchor bandage 10 to expose the adhesive layer. The outer covering layer 18 is positioned over the arterial catheter such that the catheter is positioned in the cavity of the bulbous portion of the bulbous shield. Then the outer covering layer 18 is pressed to the patient's skin so as to hold the arterial anchor bandage 10 securely in place (see FIG. 5).

When the bandage has been attached to the patient, the tube 40 extending from the circular opening 14 is led away from the crease in the patient's skin. In this regard, the tube is clipped to the tube clip 19 so that the tube will remain close to the patient's arm yet be securely positioned by the bandage 10. It will also be noted that the tube clip which can be integral with the bandage 10 serves to hold the tube in an elevated position above the crease in the patient's wrist. Moreover, it will be observed that the bandage effectively focuses the stress of bending the tube at the circular opening 14 where the tube 40 passes through the bulbous shield. As a result, there is a significant decrease in the level of discomfort that the patient experiences since movement of the catheter relative to the patient's body resulting from stress on the tube is essentially eliminated.

With the arterial anchor bandage 10 in place, the point where the arterial catheter is inserted into the skin can be visually observed and inspected at all times. Moreover, to the extent that any bodily fluids or secretions appear in the vicinity of the catheter, the absorbent layer wicks those fluids and secretions away from the wound. The air permeability characteristics of the arterial anchor bandage 10 also permit circulation of air to the region of the arterial catheter to keep the skin healthy and to promote healing.

The manner in which the arterial catheter is anchored prevents the catheter from being pulled out of the patient. Moreover, the catheter can be rotated by rotating its associated tube in order to check for positionality of the catheter. And, the stiffness of the bulbous shield firmly and accurately positions the catheter so that consistent information can be obtained from it.

Significantly, the arterial anchor bandage 10 can be applied to a patient in approximately one-half of a minute in contrast to the several minutes now required for less efficient procedures. Furthermore, the arterial anchor bandage 10 eliminates the need to suture the arterial catheter in position.

The arterial anchor bandage of the present invention provides the normal means of protection from infection in a much more convenient package than previously available, as well as additional features of caring for the catheter. Moreover, the transparent shield is extremely strong due to its shape which includes a decreasing radius in the bubble and reduces trauma to the site. Furthermore, the arterial anchor bandage allows continual visual surveillance of the site, while wicking away undesirable secretions and maintaining the preferred inclination of the catheter relative to the patient. And, the catheter is secured without the need for sutures.

It should now be apparent that there has been provided in accordance with the present invention a new and useful arterial anchor bandage which overcomes problems associated with the known procedures and which provides significant advantages in the care of critical patients. Moreover, it will be apparent to those skilled in the art that there are many variations, substitutions, and equivalents of the features of the invention described herein. Accordingly, it is expressly intended that all such modifications, variations, substitutions and equivalents which fall within the spirit and scope of the invention as defined in the appended claims be embraced thereby.

What is claimed is:

1. An arterial anchor bandage comprising:
   a bulbous element having a generally planar flange defining an oblong footprint, with a central opening and a peripheral edge fashioned from a transparent material, including a general circular opening at a predetermined elevation above the footprint sized to receive a cannula tube, a slit extending from the opening through the flange, and the flange defining an acute angle with the bulbous element at the slit;
   a layer of absorbent material under the flange having an opening generally coextensive with the central opening, and extending laterally beyond the flange;
   an outer covering having an adhesive surface and a cutout larger than the central opening but smaller than the peripheral edge of the flange, the bulbous element being received in the cutout and so that the flange is adhesively bonded to the outer covering, and the absorbent layer being adhesively bonded to the outer covering outside the peripheral edge of the flange; and
   a protective layer coextensive with the outer covering, releasable from the adhesive surface to expose the adhesive surface.

2. The arterial anchor bandage of claim 1 wherein the bulbous element has an increased thickness adjacent the slit so as to define a locally more rigid area for cannula support.

3. The arterial anchor bandage of claim 1 wherein the outer covering is recessed adjacent the slit in the bulbous element to permit application near joints of a human body.

4. The arterial anchor bandage of claim 3 wherein the outer covering includes a pair of lateral wings, each wing extending laterally in the direction transverse to the bulbous element so as to provide secure support.

5. The arterial anchor bandage of claim 1 wherein the outer covering includes means for permitting air to traverse the outer covering.

6. The arterial anchor bandage of claim 1 wherein the bulbous element, in vertical cross section, is generally elliptical with the major axis in general alignment with the circular opening to reduce optical distortion of the central opening of the footprint.

7. The arterial anchor bandage of claim 1 further including means for holding a tube connectable with a catheter.

* * * * *